United States Patent [19]

Senda

[11] 4,000,089
[45] Dec. 28, 1976

[54] ELEMENT FOR DETECTING CARBON MONOXIDE

[75] Inventor: Tamotsu Senda, Tokyo, Japan

[73] Assignee: Nohmi Bosai Kogyo Co., Ltd., Tokyo, Japan

[22] Filed: May 23, 1974

[21] Appl. No.: 472,900

[30] Foreign Application Priority Data

June 12, 1973  Japan .................... 48-65353

[52] U.S. Cl. .................... 252/514; 252/408; 252/518; 252/472; 23/232 E; 73/27 R
[51] Int. Cl.² .................... H01B 1/02
[58] Field of Search .......... 252/514, 518, 519, 472, 252/408 R, 466 PT; 23/232 E; 73/27 R, 23

[56] References Cited

UNITED STATES PATENTS

| | | | |
|---|---|---|---|
| 1,684,587 | 9/1928 | Hultman | 252/408 |
| 2,219,261 | 10/1940 | Mampke | 252/472 X |
| 2,738,257 | 3/1956 | Darby | 252/408 |
| 3,245,917 | 4/1966 | Mayo | 252/408 |
| 3,670,044 | 6/1972 | Drehman et al. | 252/472 X |
| 3,692,701 | 9/1972 | Box | 252/472 X |
| 3,794,599 | 2/1974 | Dautzenberg et al. | 252/472 X |
| 3,879,985 | 4/1975 | Maslen | 73/27 R |

FOREIGN PATENTS OR APPLICATIONS

| | | | |
|---|---|---|---|
| 477,288 | 9/1951 | Canada | 252/408 |
| 1,081,692 | 5/1960 | Germany | 252/408 |
| 1,084,049 | 6/1960 | Germany | 252/408 |

Primary Examiner—Benjamin R. Padgett
Assistant Examiner—E. Suzanne Parr
Attorney, Agent, or Firm—Michael J. Striker

[57] ABSTRACT

This invention relates to an element which can detect selectively carbon monoxide from other reducing gases contained in air. The element has a sensitive response to carbon monoxide at a comparatively low temperature and not to other reducing gases. The element has a composition comprising stannic oxide as a base material, platinum black as a catalyst and, if necessary, clay, ferric oxide or glassy substances as a sintering agent. A starting substance for stannic oxide may be stannic oxide itself or any stannic salt which is changed into stannic oxide by baking. A starting substance for platinum black may be platinum black itself or any platinum salt which is changed into platinum black by baking. The above starting substances are thoroughly mixed and baked to form a detecting element. The element may be used as a lump by itself, but it is convenient that it is used as a film of the element baked on a heat-resisting insulating material such as an alumina ceramics, quartz glass or boracic silica glass.

17 Claims, 5 Drawing Figures

ELEMENT FOR DETECTING CARBON MONOXIDE

This invention relates to an element which can detect selectively carbon monoxide from other reducing gases contained in air.

Therefore, one object of this invention is to provide an element for detecting selectively carbon monoxide from other reducing gases in air at a comparatively low temperature.

Another object of this invention is to provide an element for detecting selectively carbon monoxide from other reducing gases in air to prevent disaster by poisoning and fire.

When n-type semi-conductors of metal oxides are left in air containing any reducing gas, they adsorb such a gas on their surface and consequently there occurs a change in their electric resistance. This phenomenon has been applied to prepare an element for detecting reducing gases. But the n-type semi-conductors have not a capability for detecting selectively carbon monoxide alone from various gases in air. At present, the metal oxides which are applied for detection of reducing gases are mainly stannic oxide $SnO_2$ and zinc oxide $ZnO$. When these materials are used as such for the element, they are not sensitive to reducing gases unless they are left at a high temperature such as above 250° C for an element consisting of only $SnO_2$ and above 500° C for an element consisting of only $ZnO$. Therefore, in order to intensify the sensitivity for reducing gases, palladium chloride or aurichloric acid was used as a catalyst for the semi-conductor as described above. But it has been proved that the addition of such materials is not at all effective for selective detection of carbon monoxide.

This invention has been conceived to prepare an element for detecting selectively and sensitively carbon monoxide at a comparatively low temperature. Briefly stated in accordance with this invention, there is provided an element for detecting selectively carbon monoxide which has a composition comprising stannic oxide $SnO_2$ as a base material, platinum black as a catalyst and, if necessary, clay, ferric oxide or a glassy substance as a sintering agent. A starting substance for said stannic oxide may be stannic oxide itself or any stannic salt which is changed into stannic oxide by baking. A starting substance for platinum black may be platinum black itself or a platinum salt which is changed into platinum black by baking. The above starting substances are thoroughly mixed and baked to form a detection element. The platinum black or the decomposed platinum black is assumably distributed between the particles of stannic oxide so as to endow the capability of detecting selectively carbon monoxide to the baked mixture. This element may be used as a lump by itself, but it is convenient that it is used as a film of the element baked on a heat-resisting insulating material such as alumina ceramics, quartz glass or boracic silica glass.

This invention will be better understood and other objects and additional advantages of this invention will become apparent upon perusal of the following description in connection with the drawings, in which FIG. 1 is a graphic chart showing the relationship between the electric resistance and the temperature in regard to an element of stannic oxide with addition of palladium chloride as a catalyst;

Figure 5:
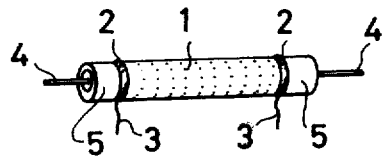
FIG. 5 is a perspective side view of an element of this invention as baked onto a cylindrical alumina ceramic tube.

The following are examples exhibiting the practice of the invention:

Example 1: Stannic oxide is used here as a base material, and chloroplatinic acid $H_2PtCl_6.2H_2O$ as a catalyst and clay as a sintering agent are added thereto. The composition has a ratio of 80 % stannic oxide, 10 % chloroplatinic acid and 10 % clay by weight. Since chloroplatinic acid is deliquescent, the preferable procedure is to first mix stannic oxide and clay thoroughly in a mortar for 30 minutes and then to add chloroplatinic acid and a small amount of water to them. After kneading enough, the mixture is coated thinly onto an alumina ceramic tube as shown in FIG. 5, which is left in air for 30 minutes thereafter to be dried. Then the coated film on the ceramic tube is sintered in an electric oven for 15 minutes in an oxidizing atmosphere and at a temperature of 900° C.

Example 2: Stannic bromide $SnBr_4$ and bromoplatinic acid $H_2PtBr_6$ are employed in the ratio 95 : 5 by weight and dissolved in hydrochloric acid. The above solution is coated with a brush over the outer surface of an alumina ceramic tube 5 as shown in FIG. 5, which is 10mm in length, 1.5mm in inner diameter and 2.5mm in outer diameter. Then said tube 5 is sintered from an hour in an oxidizing atmosphere at a temperature of 600° C to form a film-like sensitive element 1. Both ends of the element 1 are coated with silver paste and heated at a temperature of 500° C for 10 minutes, then silver electrodes 2 are formed. Leads 3 are connected to the silver electrodes 2 and, if necessary, electric heating wire 4 is made to pass through the hollow interior of the tube 5.

Example 3: An element is formed of stannic oxide $SnO_2$ with addition of platinum sulphate $Pt(SO_4)_2.4-H_2O$ as a catalyst and clay as a sintering agent. The composition of the element is in the weight ratio of 82 % stannic oxide, 8 % platinum sulphate and 10 % clay. The mixture is well kneaded with addition of a small amount of water and coated thinly over the outer surface of an alumina ceramic tube and finally sintered for 15 minutes in an oxidizing atmosphere at a temperature of 900° C.

Example 4: Platinum black as a catalyst and clay as a sintering agent are added to a base material of stannic oxide. The weight ratio of the composition is 85.5 % stannic oxide, 4.5 % platinum black and 10 % clay. After the composition is thoroughly mixed in a mortar, it is well kneaded with addition of a small amount of water. As shown in FIG. 5, an alumina ceramic tube 5 which is coated with the mixture is sintered for 30 minutes at a temperature of 400° C.

Under the condition that the element of this invention was in air containing each of various reducing gases, the sensitivity of it was measured. The electric resistance value and the resistance ratio are as shown in Table 1. Here the temperature of the element is 25° C and the content of each reducing gas in the air is 1,000 ppm. The electric resistance value in clean air is 3 M$\Omega$ and the resistance ratio is calculated as follows;

$$\text{Resistance ratio} = \frac{\text{resistance value in clean air}}{\text{resistance value in air containing a reducing gas}}$$

Table 1

| Reducing gas | Electric resistance (M$\Omega$) | Resistance ratio |
| --- | --- | --- |
| Carbon monoxide CO | 0.02 | 150 |
| Hydrogen $H_2$ | 1.9 | 1.6 |
| Methane $CH_4$ | 3.0 | 1.0 |
| Acetylene $C_2H_2$ | 2.0 | 1.5 |
| Ethylene $C_2H_4$ | 2.2 | 1.4 |
| Ethane $C_2H_6$ | 3.0 | 1.0 |
| Propane $C_3H_8$ | 3.0 | 1.0 |
| Butane $C_4H_{10}$ | 3.0 | 1.0 |
| Methyl alcohol $CH_3OH$ | 2.5 | 1.2 |
| Ethyl alcohol $C_2H_5OH$ | 2.5 | 1.2 |
| Ethyl ether $(C_2H_5)_2O$ | 2.6 | 1.2 |
| Formaldehyde HCHO | 2.6 | 1.2 |
| Benzene $C_6H_6$ | 2.7 | 1.1 |
| Toluene $CH_3 \cdot C_6H_5$ | 2.7 | 1.1 |

The results of measurements shown above indicate that the electric resistance value of the element of this invention in air containing such hydrocarbons as methane, ethane, propane or butane is scarcely different from that in clean air. They indicate further that the electric resistance ratio in air containing hydrogen, acetylene, ethylene, methyl alcohol or ethyl alcohol are as small as 1/100 in comparison with that in air containing carbon monoxide. Therefore, whenever any reducing gas other than carbon monoxide is contained in air, the existence of such a gas may be disregarded in detecting carbon monoxide.

Figure 1:
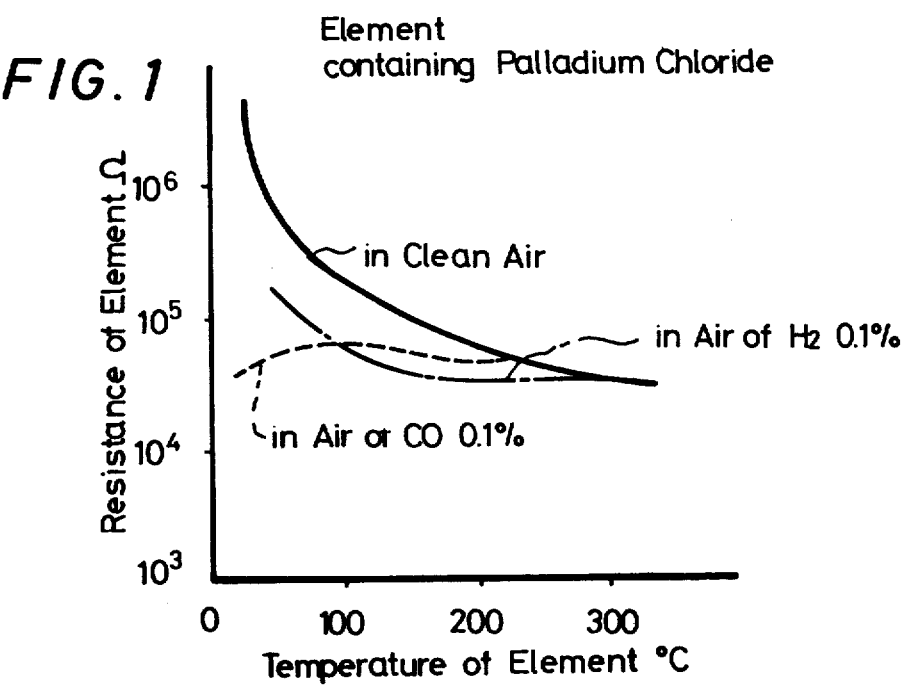
Figure 2:
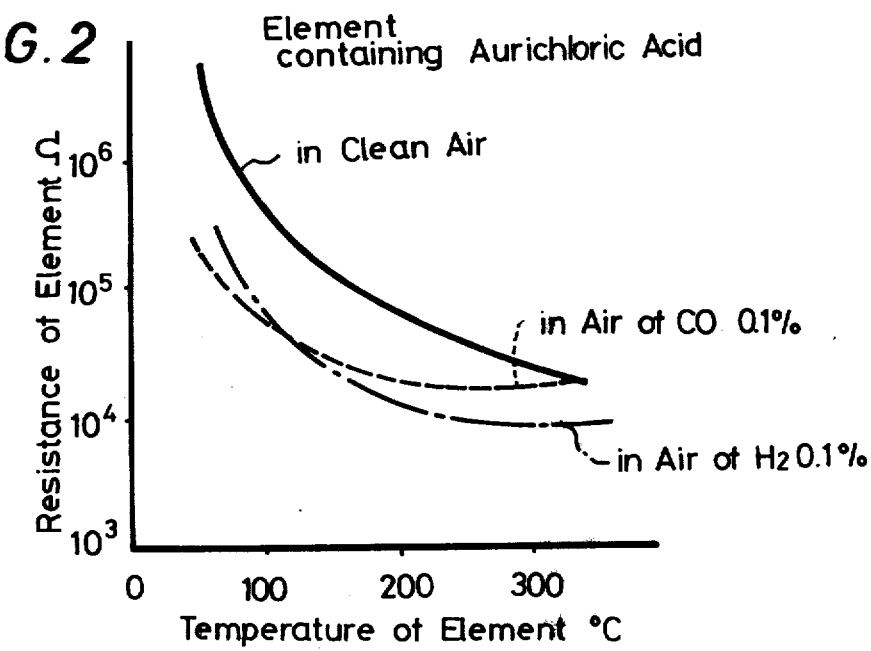
FIG. 2 is a graphic chart showing the relationship between the electric resistance and the temperature in regard to another element of stannic oxide with addition of aurichloric acid as a catalyst.
Figure 3:
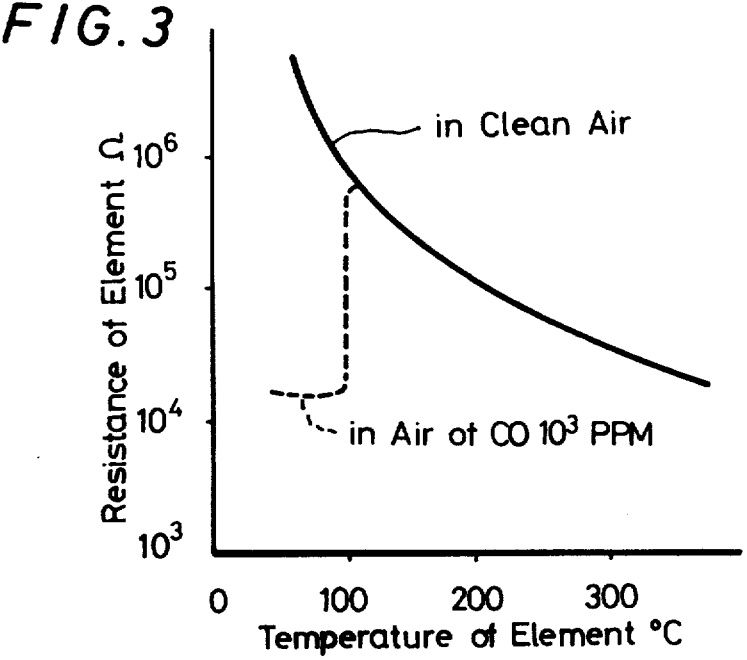
FIG. 3 is a graphic chart showing the relationship between the electric resistance and the temperature in regard to an element of this invention.
Figure 4:
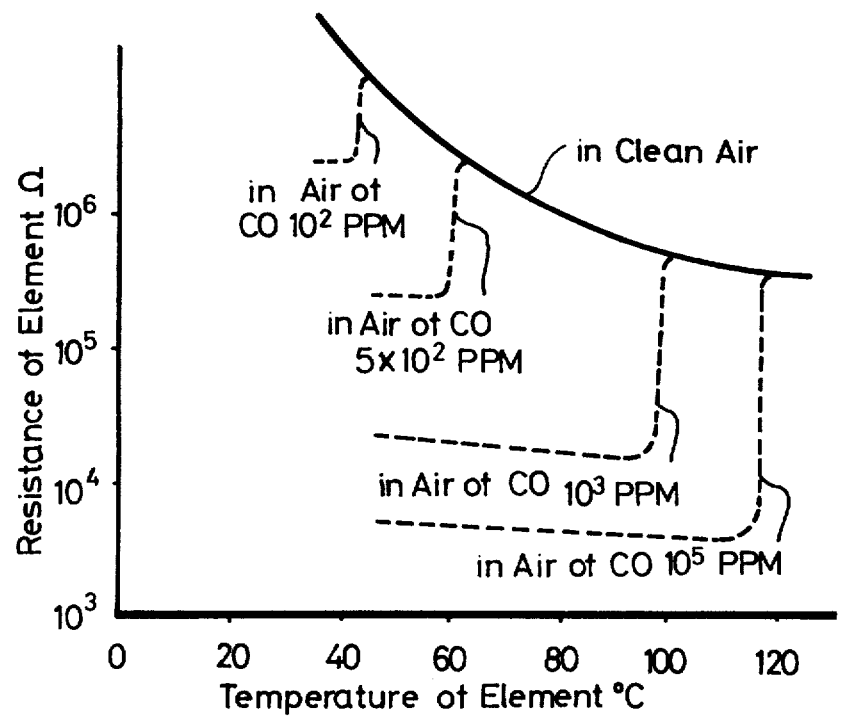
FIG. 4 is a graphic chart showing the relationship between the electric resistance and the temperature in regard to an element of this invention in air with various contents of carbon monoxide.

The electric resistances of the element of this invention and other elements of stannic oxide containing palladium chloride and aurichloric acid, respectively, as a catalyst were measured in air containing 1,000 ppm of carbon monoxide or hydrogen gas, respectively, and the appended graphic charts were prepared. FIG. 1 shows the case of the element using palladium chloride as a catalyst, FIG. 2 shows the case of the element using aurichloric acid as a catalyst and FIG. 3 shows the case of this invention. It is proved from FIGS. 1 and 2 that the elements are sensitive to hydrogen and carbon monoxide to an equal degree, respectively, and therefore, that they have no capability for selective detection of both gases and have no characteristic that the resistance value changes suddenly at a certain temperature. It is proved on the other hand from FIG. 3 that the element of this invention is sensitive to carbon monoxide alone and not to any other reducing gases and there exists a special temperature at which the resistance value changes suddenly. FIG. 4 is a graph which shows the relationship between the resistance of the element and the temperature of element when the element of this invention is left in air having various contents of carbon monoxide. The graph has proved that if the temperature of the element is fixed at 60° C, the sudden change of electric resistance value occurs at the content of 500 ppm of carbon monoxide in air, and it is insensitive to a content below 500 ppm of carbon monoxide and is sensitive to a content above 500 ppm of carbon monoxide. Conversely, if the content of carbon monoxide in air is fixed at 500 ppm and the element of this invention is brought to the temperature of 60° C either by heating or cooling, a sudden change of electric resistance value occurs. When the content of carbon monoxide in air increases further, the temperature at which the electric resistance of the element meets with a sudden change shifts to the higher side. Therefore, the element of this invention responds selectively to carbon monoxide having a content higher than a certain content at a temperature lower than a certain temperature where a sudden change of electric resistance value occurs. And its response to carbon monoxide is quick, and when carbon monoxide vanishes from air, the element resistance value returns rapidly to that in clean air. In the cases of the conventional elements, when they come in contact with any reducing gas contained in air at low temperature, the change of the resistance valve does not occur immediately and when the reducing gas vanishes from air, the resistance value does not rapidly return to that in clean air. Namely they are slow with respect to their response to the reducing gas and require a long time to restore their normal state. Therefore in order to improve the response to the reducing gas, a restoring agent has been used for the conventional elements. The element of this invention does not need any restoring agent. As stated hereinbefore, this invention uses platinum black or platinic salt as a starting substance for a catalyst which changes to platinum black when baked together with the base material of stannic oxide. An experiment has been performed in air containing 500 ppm of carbon monoxide to determine in what manner the content of platinum black in the element affects the electric resistance ratio for carbon monoxide. The results are shown in Table 2.

Table 2

| Measure No. | $SnO_2$ % | Pt % | Resistance ratio |
| --- | --- | --- | --- |
| 1 | 99.8 | 0.2 | 1.92 |
| 2 | 99.5 | 0.5 | 16.88 |
| 3 | 98.5 | 1.5 | 51.92 |
| 4 | 96.9 | 3.1 | 61.33 |
| 5 | 89.0 | 11.0 | 57.10 |
| 6 | 66.9 | 33.1 | 61.50 |

It has been proved from the above table that the effective content of platinum in the element of this invention ranges from 0.5 % to upwards of 33.1 %. However, an excessively high platinum content deviates from the scope of catalyst and is not recommendable from the point of view of economy of the element. It is desirable that the catalyst be excellent in its action when used in a small amount. In the case of this invention, it is proper that the content of platinic salt or platinum black ranges from 0.5 to 10 % by weight by calculating in terms of metallic platinum.

From the foregoing description, it will be understood that the element of the invention has such a remarkable property that it provides a highly effective means to detect carbon monoxide contained in gas exhausted from motor vehicles, exhaust and combustion gas from factories and gas generated from fire disasters.

What I claim is:

1. A composition for the detection of carbon monoxide comprising stannic oxide as a base metal and platinum comprising platinum black as an agent for imparting to said composition the ability to selectively detect the presence of carbon monoxide, said platinum constituting a minimum of about 0.5 percent by weight of said composition.

2. A composition for the detection of carbon monoxide comprising stannic oxide or stannic salts capable of changing to stannic oxide upon baking, as a base material; and platinum black or platinum salts that change to platinum black upon baking as an agent for imparting to said composition the ability to selectively detect the presence of carbon monoxide, said platinum black or said platinum salts constituting a minimum of about 0.5 percent by weight of said composition as calculated in terms of metallic platinum.

3. The composition of claim 2, comprising a maximum of about 10 percent by weight of said platinum.

4. The composition of claim 2, comprising at least one member of the group of sintering agents consisting of clay, ferric oxide and glassy substances.

5. A composition for the detection of carbon monoxide, comprising stannic oxide as a base material; and platinum black as an agent for imparting to said compostion the ability to selectively detect the presence of carbon monoxide, said platinum black constituting between about 0.5 and 10 percent by weight of said composition.

6. A method of making compositions for the detection of carbon monoxide, comprising forming a mixture which includes a first substance selected from the group consisting of stannic oxide and stannic salts capable of changing to stannic oxide upon baking, and a second substance selected from the group consisting of platinum black and platinum salts that change to platinum black upon baking, said second substance constituting a minimum of about 0.5 percent by weight of said mixture as calculated in terms of metallic platinum; and heating said mixture so as to obtain a composition which includes stannic oxide as a base material and platinum black or platinum salts as an agent for imparting to said composition the ability to selectively detect the presence of carbon monoxide.

7. The method of claim 6 wherein said heating is carried out in an oxidizing atmosphere when baking the composition to form a detector element.

8. The method of claim 6, wherein said mixture is heated to temperatures between 400° and 900° C, when baking the composition to form a detector element.

9. The method of claim 6, wherein said mixture is heated for a period between 15 and 60 minutes, when baking the composition to form a detector element.

10. The method of claim 6, wherein said mixture is heated to temperatures between 400° and 900° C for a period of about 15 to 60 minutes in an oxidizing atmosphere, when baking the composition to form a detector element.

11. The method of claim 6, wherein said heating comprises sintering said mixture.

12. The method of claim 6, wherein said second substance constitutes a maximum of about 10 percent by weight of said mixture as calculated in terms of metallic platinum.

13. The method of claim 6, wherein the platinum in said composition comprises platinum black.

14. The method of claim 6, wherein said forming comprises kneading said mixture.

15. The method of claim 6, wherein said forming comprises incorporating a sintering agent in said mixture.

16. The method of claim 15, wherein said sintering agent comprises a substance from the group consisting of clay, ferric oxide and glassy substances.

17. A method of making compositions for the detection of carbon monoxide, comprising forming a mixture which includes a first substance selected from the group consisting of stannic oxide and stannic salts capable of changing to stannic oxide upon baking, and a second substance selected from the group consisting of platinum black and platinum salts that change to platinum black upon baking, said second substance constituting between about 0.5 and about 10 percent by weight of said mixture as calculated in terms of metallic platinum; and heating said mixture to temperature between about 400° and 900° C for a period of about 15 to 60 minutes in an oxidizing atmosphere, when baking the composition to form a detector element, so as to obtain a composition which includes stannic oxide as a base material and platinum black as an agent for imparting to said composition the ability to selectively detect the pressence of carbon monoxide.

* * * * *